United States Patent [19]

Briody

[11] 4,085,133

[45] Apr. 18, 1978

[54] PREPARATION OF MONOPEROXYPHTHALIC ACID

[75] Inventor: Robert G. Briody, Corpus Christi, Tex.

[73] Assignee: PPG Industries, Inc., Pittsburgh, Pa.

[21] Appl. No.: 744,561

[22] Filed: Nov. 24, 1976

[51] Int. Cl.² .......................................... C07C 179/10
[52] U.S. Cl. ............................................... 260/502 R
[58] Field of Search ........................ 260/502 R, 502 A

[56] References Cited

U.S. PATENT DOCUMENTS

| | | | |
|---|---|---|---|
| 2,273,744 | 2/1942 | Reichert | 260/502 R |
| 3,284,491 | 11/1966 | Koroch et al. | 260/502 R |
| 3,510,512 | 5/1970 | Jourdan-Laforte | 260/502 R |

*Primary Examiner*—James O. Thomas, Jr.
*Assistant Examiner*—Werren B. Lone
*Attorney, Agent, or Firm*—Edward J. Whitfield; Roger S. Benjamin

[57] ABSTRACT

Stable monoperoxyphthalic acid is prepared by reacting phthalic anhydride with a stoichiometric excess of concentrated hydrogen peroxide in the absence of basic catalyst in liquid halogenated hydrocarbon medium in which the monoperoxyphthalic acid product is insoluble.

4 Claims, No Drawings

4,085,133

PREPARATION OF MONOPEROXYPHTHALIC ACID

BACKGROUND OF THE INVENTION

Monoperoxyphthalic acid (MPA) has low detonability, good water solubility and general utility as an oxidant and bleach.

MPA may be prepared as a solution in various solvents by the reaction of hydrogen peroxide and phthalic anhydride with or without a basic catalyst (see; Swern, Daniel, ed. *Organic Peroxides* Wiley-Interscience Publ., New York, New York 1970 pages 424–427 and U.S. Pat. No. 2,273,774 to Reichert, J.S.).

Synthesis of MPA in non-solvents using basic catalyst permits convenient recovery of product as a precipitate (see; U.S. Pat. No. 3,510,512 to Jourdan-Laforte, E.).

Both solvent and base catalyzed non-solvent reaction mediums for MPA synthesis have disadvantages. Processes which employ solvents require the extra step of solvent removal or product extraction. Processes which use basic catalysts impart instability to the MPA product and subsequent attempts to neutralize the catalyst do not give the desired improvement in stability.

THE INVENTION

This invention concerns the preparation of stable monoperoxyphthalic acid. Moreover, this invention is a method of conveniently preparing MPA without the use of basic catalyst or attendant catalyst removal steps.

The process of this invention is practiced by reacting phthalic anhydride with concentrated hydrogen peroxide in the absence of a basic catalyst in a liquid halogenated hydrocarbon medium in which the MPA is insoluble.

It is a discovery of this invention that a combination of reaction conditions, proportions of reactants, and product purification will result in an MPA product of unexpectedly high stability.

Specifically this invention concerns the discovery that MPA of high stability is prepared (1) in the absence of basic catalyst, (2) using a stoichiometric excess of concentrated hydrogen peroxide, (3) operating in an agitated liquid reaction medium which is a non-solvent for MPA, (4) with post-synthesis removal of residual $H_2O_2$ without addition of acid or base.

Reactants, reaction media, and the reaction zone should be free of catalytically effective amounts of basic substances. Generally, catalysts to assist the reaction of phthalic anhydride and hydrogen peroxide are compounds having a pH above 8 at 0.1 moles per liter or less aqueous concentration. Such compounds include solids, liquids and gases which may be dispersed or dissolved in the reaction medium. Examples of basic catalyst species and specific basic catalysts are alkali-metal hydroxides, sodium hydroxide, alkaline-earth hydroxides, alkaline-earth oxides, magnesium oxide, alkali-metal carbonates, ammonium hydroxide, pyridine.

Hydrogen peroxide is insoluble in the reaction medium and is used in the uncatalyzed process of this invention in concentrated form and in excess to effect a practical rate of reaction. "Concentrated hydrogen peroxide" denotes aqueous hydrogen peroxide having at least 65 weight percent $H_2O_2$ and preferably over 85 weight percent $H_2O_2$.

One mole of hydrogen peroxide reacts with one mole of phthalic anhydride. Hydrogen peroxide should be present in the reaction zone in at least a 20 mole percent stoichiometric excess over the quantity required. Preferably, concentrated hydrogen peroxide is used in at least a 60 mole percent excess. There is no upper limit to the excess of hydrogen peroxide which may be present. Beside assuring adequate conversions (above 70%) and reasonable reaction times the excess peroxide present during the reaction appears to act beneficially by giving increased stability to the final MPA product.

Criteria for the selection of reaction medium are that it (1) not react with the MPA product or reactants, principally hydrogen peroxide, under conditions of synthesis and (2) that the medium have low solubility for MPA. Solubility levels of less than one percent by weight under conditions of MPA removal are satisfactory for operation of the claimed invention. Additionally, it is desirable that the reaction medium be a solvent for the phtalic anhydride reactant and a non-solvent for the MPA. This dual solubility characteristic will permit retention of the unreacted starting material while concurrently assisting precipitation of the desired product.

Halogenated hydrocarbons are particularly desirable because of their inertness and ability to act as non-solvents for MPA. Examples of suitable reaction medium are the halogenated solvents referred to in U.S. Pat. No. 3,510,512 (Col. 2) to Jourdan-Laforte, E. which are incorporated herein by reference. 1,2-dichloroethane has been found especially useful as reaction medium.

The phthalic anhydride reactant may be commercial or reagent grade. If desired, the phthalic anhydride may be purified by recrystallization or sublimation. Generally, phthalic anhydride of over 90 weight percent purity may be used in the process. To facilitate reaction it is advantageous to grind the phthalic anhydride to a convenient particle size, typically 10 to 325 mesh.

Reaction temperature in the absence of catalyst must be at least 35° C. Preferably, the reaction is initiated at a temperature about 45° C. At the opposite extreme it is suggested that the MPA synthesis be conducted at a temperature not above 70° C. to avoid undue decomposition of the MPA product.

Typical reaction times at the preferred temperatures are between one and ten hours. It is necessary to constantly agitate the reactants and reaction medium as by stirring and shaking to adequately disperse the immiscible aqueous hydrogen peroxide phase and make it available for reaction in the reaction medium.

The conclusion of the reaction may be determined by analysis for unreacted hydrogen peroxide and MPA. MPA product may initially be separated from the reaction medium by decanting the reaction medium. Alternately, the MPA may be drained or pumped from the lower portion of the reaction medium. If desired, the separation of MPA product from the reaction medium may be assisted by filters or centrifugal devices.

Since basic catalysts are not used in the preparation of MPA according to the process of this invention, it is unnecessary to employ a post-synthesis acid treatment to remove residual base. Every effort should be made to avoid contamination of the product by addition of either acids or bases at the conclusion of the reaction since these materials are a likely source of product instability.

The MPA product withdrawn from the reaction medium is dried of entrained water, hydrogen peroxide, and reaction medium. Drying may be accomplished simply by passing a stream of dry gas through the product. Another method is to vaporize the entrained materials in a vaccum chamber. It is preferable to conduct the vaporization of these contaminants at near ambient or lower temperatures to avoid unnecessary decomposition of the MPA. Residual hydrogen peroxide appears to increase the instability of the MPA product. The final level of hydrogen peroxide should be less than 0.35 weight % if a stable product is desired.

Phthalic acid will occur to some extent in the MPA product since it is the decomposition product of monoperoxyphthalic acid as well as the reaction product of phthalic anhydride with the water content of the hydrogen peroxide reactant. Normally the presence of phthalic acid will not affect the product's utility and it need not be separated.

The stability of the MPA product is measured as the percent weight loss of MPA per day at 60° C. The 60° C decomposition temperature is a more rigorous standard of stability than room temperature decomposition rates and provides an estimate of decomposition under conditions encountered in shipment of commercial products (e.g., boxcar storage under hot sun). For the purpose of this invention the designation of "stable" MPA product is taken to be a decomposition rate of less than 3.0 weight percent per day at 60° C.

EXAMPLE I

This example describes the preparation of monoperoxyphthalic acid in halogenated hydrocarbon medium using ammonium hydroxide catalyst and various degrees of post-synthesis catalyst neutralization:

0.5 moles of phthalic anhydride, 0.6 moles of 70 weight percent $H_2O_2$, and 2.2 ml. of concentrated ammonium hydroxide catalyst were added to 1214 grams of freshly distilled ethylene dichloride reaction medium. The reaction mixture was rapidly stirred and maintained at a temperature of 40° C. After 10 minutes a viscous lower layer appeared which rapidly changed to a solid. After an additional four minutes the reaction mixture was cooled and concentrated sulfuric acid added drop by drop. Stirring was continued for 30 minutes, the mixture was filtered and the solid residue dried overnight in a vacuum oven at room temperature.

Stability of monoperoxyphthalic product was determined by placing samples into tared vials and storing the vials at selected temperatures. The monoperoxyphthalic acid content was analyzed iodometrically. Decomposition rate was calculated as weight percent monoperoxyphthalic acid lost per day. The test results are displayed in Table I below.

Table I
Stability of Monoperoxyphthalic Acid Samples Containing Various Ratios of Ammonium Hydroxide Catalyst and Sulfuric Acid Neutralization Agent

| Sample No. | Equivalents $H_2SO_4$/ Equivalents $NH_4OH$ | Weight % Decomposition/Day | | |
|---|---|---|---|---|
| | | 40° C | 50° C | 60° C |
| 1 | 0.82 | 1.7 | 4.0 | 13.9 |
| 2 | 0.96 | 1.3 | 2.4 | 13.1 |
| 3 | 1.15 | 0.6 | 1.8 | 10.1 |
| 4 | 1.40 | 0.9 | 2.9 | 8.2 |
| 5 | 1.95 | 0.4 | 1.5 | 8.1 |

Example I illustrates that neutralization of base catalyzed reaction medium improves the stability of MPA product. However, neither neutralization nor the use of excess acid is productive of stable MPA.

EXAMPLE II

This example describes the preparation of monoperoxyphthalic acid in halogenated hydrocarbon medium using various basic catalysts and postsyntheses neutralization:

Into a 600 ml. glass beaker was placed 302 ml. of ethylene dichloride reaction medium, 74.06 gms. of phthalic anhydride, concentrated hydrogen peroxide, and basic catalyst. The hydrogen peroxide was added gradually over a 10 to 22 minute period. The reaction mixture was raised to reaction temperature and stirred for a period of hours. Thereafter, neutralization agent was added and stirring continued. The reaction mixture was cooled, filtered, pressed dry, and dried under vacuum. Reaction conditions and experimental results are set out in Table II below:

Example II illustrates that MPA produced by a variety of basic catalysts and neutralization agents is not stable.

TABLE II

| Sample No. | $H_2O_2$ Gms. (90.01 Wt.%) | Catalyst | Quantity Catalyst Gms. | Yield % MPA | Neutralization Agent | Max. Reaction Temp. °C | Residual % $H_2O_2$ in Sample | Decomposition Rate Wt.%/Day at 60° C | Time, Hrs. | |
|---|---|---|---|---|---|---|---|---|---|---|
| | | | | | | | | | RX | Neutralizaton |
| 6 | 28.4 | 25.45 wt% | 0.8663 | 77.0 | 0.7829 Gms. Acetic Acid | 41 | 0.15 | Approx. 20 | 3.1 | 1 |
| 7 | 28.3 | MgO | 2.028 | 81.5 | 5.174 Gms. $H_2SO_4$ | 39.8 | 0.2 | 11.6 | 3 | 1 |
| 8 | 28.3 | MgO | 2.03 | 83.2 | 6.14 Gms Acetic Acid | 38 | 0.34 | 4.2 | 3 | 1 |
| 9 | 28.4 | Pyridine | 0.253 | 84.4 | 0.200 Gms. Acetic Acid | 36.5 | 0.10 | 4.8 | 6 | 1 |

EXAMPLE III

This example illustrates the preparation of stable monoperoxyphthalic acid in accordance with the practice of this invention:

300 grams of distilled ethylene dichloride and 0.5 mole phthalic anhydride were placed in a 600 ml. beaker. The beaker was heated to 55°-57° C in an oil bath and then $H_2O_2$ added dropwise to the reaction mixture. No basic catalyst was used in the monoperoxyphthalic acid preparation.

Stirring was continued for 6 hours. Thereafter, the beaker was cooled, the solid product filtered, pressed dry, and dried under vacuum. Reaction conditions and experimental results are set out in Table III.

TABLE III

| Sample No. | Phthalic Anhydride Assay % | $H_2O_2$ Assay % | Moles | MPA Product,% Residual $H_2O_2$ | MPA % | Yield % | Decomposition Rate Wt.%/Day at 60° C |
|---|---|---|---|---|---|---|---|
| 10 | 94.8 | 88.7 | .093 | .09 | 82.4 | 84.4 | 2.1 |
| 11 | 97.8 | 88.7 | .93 | .10 | 83.8 | 82.4 | 1.9 |

TABLE III-continued

| Sample No. | Phthalic Anhydride Assay % | $H_2O_2$ Assay % | $H_2O_2$ Moles | MPA Product,% Residual $H_2O_2$ | MPA % | Yield % | Decomposition Rate Wt:%/Day at 60° C |
|---|---|---|---|---|---|---|---|
| 12 | 97.9 | 89.3 | .90 | .04 | 85.6 | 84.6 | 1.6 |

It is to be understood that although the invention has been described with specific references and specific details of embodiments thereof, it is not intended to be so limited since changes and alterations therein may be made which are within the full intended scope of this invention as defined by the appended claims.

I claim:

1. A process for preparing thermally stable, solid monoperoxyphthalic acid comprising reacting, in a liquid halogenated hydrocarbon reaction medium, phthalic anhydride with an aqueous hydrogen peroxide solution having a hydrogen peroxide content of at least 65 percent by weight at a molar ratio of hydrogen peroxide to phthalic anhydride of at least 1.2 to 1, said liquid halogenated hydrocarbon being a solvent for the phthalic anhydride and a non-solvent for the monoperoxyphthalic acid, precipitating monoperoxyphthalic acid and recovering a solid monoperoxyphthalic acid having a decomposition rate of less than 3.0 weight percent per day at 60° C., said reaction being conducted with agitation at a temperature of between 35° C. and 70° C., in the absence of a basic catalyst and in the absence of the addition of acids or bases after completion of the reaction.

2. The process of claim 1 wherein the halogenated hydrocarbon is ethylene dichloride.

3. The process of claim 1 wherein the molar ratio of hydrogen peroxide to phthalic anhydride is at least 1.6 to 1.

4. The process of claim 1 wherein the hydrogen peroxide solution has a hydrogen peroxide content of over 85 weight percent.

* * * * *